(12) United States Patent
Kubacki (10) Patent No.: US 7,874,324 B2
(45) Date of Patent: Jan. 25, 2011

(54) METHODS, RACK AND DEVICE FOR PREPARING SAMPLES FOR ANALYSIS

(75) Inventor: Michel Kubacki, Louvres (FR)

(73) Assignee: Gilson, Inc., Middleton, WI (US)

( * ) Notice: Subject to any disclaimer, the term of this patent is extended or adjusted under 35 U.S.C. 154(b) by 0 days.

(21) Appl. No.: 12/506,600

(22) Filed: Jul. 21, 2009

(65) Prior Publication Data

US 2009/0277286 A1    Nov. 12, 2009

Related U.S. Application Data (62) Division of application No. 10/544,158, filed as application No. PCT/EP2004/002028 on Feb. 2, 2004, now Pat. No. 7,610,941.

(30) Foreign Application Priority Data

Feb. 3, 2003    (EP) .................................. 03290264

(51) Int. Cl.
    B65B 43/42    (2006.01)
    G01N 21/00    (2006.01)
(52) U.S. Cl. .................... 141/237; 141/65; 141/234; 422/63; 422/65
(58) Field of Classification Search .............. 141/2, 141/4–8, 65, 98, 234, 237, 329; 422/63, 422/65, 68.1, 99, 100
    See application file for complete search history.

(56) References Cited

U.S. PATENT DOCUMENTS

| | | | |
|---|---|---|---|
| 3,568,735 A * | 3/1971 | Lancaster | 141/238 |
| 4,472,352 A | 9/1984 | Quesneau et al. | |
| 5,260,028 A | 11/1993 | Astle | |
| 5,770,157 A | 6/1998 | Cargill et al. | |
| 6,033,911 A * | 3/2000 | Schultz et al. | 436/49 |
| 6,143,252 A * | 11/2000 | Haxo et al. | 506/40 |
| 6,240,984 B1 | 6/2001 | Fawcett et al. | |
| 6,464,943 B1 * | 10/2002 | Yiu | 422/100 |

(Continued)

FOREIGN PATENT DOCUMENTS

FR    2 758 188    7/1998

(Continued)

OTHER PUBLICATIONS

First Office Action issued in Chinese Patent Application No. 200480008889.2 issued Apr. 17, 2009.

(Continued)

Primary Examiner—Timothy L Maust
(74) Attorney, Agent, or Firm—Foley & Lardner LLP (57) ABSTRACT

A rack for preparing samples for analysis is provided. The rack includes a frame, a sliding assembly, a first and a second receptacle mounted in the frame underneath the sliding assembly; and means for selectively connecting each receptacle with a vacuum source. The sliding assembly is mounted for sliding in the frame and is provided with a plate having a plurality of columns for receiving samples through an upper opening of the columns. The sliding assembly is movable between a first position above the first receptacle and a second position above the second receptacle. The sliding assembly is provided with engagement means for a needle, wherein the engagement means are located outside the columns.

16 Claims, 7 Drawing Sheets

U.S. PATENT DOCUMENTS

| | | | |
|---|---|---|---|
| 6,517,783 B2 | 2/2003 | Horner et al. | |
| 6,846,456 B2 * | 1/2005 | Acosta et al. | 422/65 |
| 7,610,941 B2 * | 11/2009 | Kubacki | 141/8 |

FOREIGN PATENT DOCUMENTS

| | | |
|---|---|---|
| WO | WO 98/41875 | 9/1998 |
| WO | WO 00/08472 | 2/2000 |
| WO | WO 00/50171 | 8/2000 |

OTHER PUBLICATIONS

Second Office Action issued in Chinese Patent Application No. 200480008889.2 issued Oct. 16, 2009.

English translation of Japanese Office Action issued in corresponding Japanese Patent Application No. 2006-501978 mailed Feb. 10, 2009.

International Search Report and Written Opinion issued in PCT/EP2004/002028 mailed Jun. 25, 2004.

International Preliminary Report on Patentability issued in PCT/EP2004/002028 issued Aug. 5, 2005.

Preliminary Rejection issued in Korean Patent Application No. 10-2005-7014277 and dated Jul. 21, 2010, (English translation provided).

Restriction Requirement issued in U.S. Appl. No. 10/544,158 and mailed on Sep. 30, 2008.

US Notice of Allowance issued in U.S. Appl. No. 10/544,158 and mailed on Apr. 17, 2009.

Decision of Rejection issued in Chinese Patent Application No. 200480008889.2 and dated Aug. 2, 2010.

* cited by examiner

FIG_10

FIG_11

FIG_12

FIG_13

METHODS, RACK AND DEVICE FOR PREPARING SAMPLES FOR ANALYSIS

CROSS REFERENCE TO RELATED APPLICATION

This application is a divisional of U.S. patent application Ser. No. 10/544,158, now U.S. Pat. Ser. No. 7,610,941, filed Oct. 14, 2005, as a National Phase entry from PCT/EP04/02028, filed Feb. 2, 2004, and which claims priority under the Paris Convention to European Application No. 03290264.5, filed Feb. 3, 2003, the disclosures of which are incorporated by reference in their entirety.

FIELD

This invention relates to methods of preparing samples for analysis.

This invention also relates to a rack and a device for preparing biological samples for analysis, e.g. by chromatography.

According to a known practice of such preparation, a plate is provided with an array of parallel columns, typically 8×12=96 columns having a large upper opening and a narrow, funnel-like' lower opening. A stationary phase—or a solid phase—is provided at a certain level within each column.

The preparation steps, forming the so-called "solid-phase extraction" method, comprise a conditioning step consisting in causing a conditioning liquid to flow through the stationary phase, a loading step consisting in introducing the samples into the respective columns, one or more washing steps for eliminating from the columns, those components of the samples which are not useful for the analysis, and finally the elution consisting in transferring the useful content of each column into a respective collect tube or well, respectively. Thereafter, the content of each collect tube will be analyzed, e.g. by chromatography.

WO 00/50 171-A1 discloses a device for preparing samples for analysis in which the plate provided with the columns is mounted within a carriage which is slidable within a frame for movement into a position above a drain receptacle and a position above a collect receptacle. The conditioning, loading and washing steps are performed above the drain receptacle. Thereafter, the carriage is moved into its position above the collect receptacle and the collecting step is performed.

The plate is covered with a leak-tight membrane which seals the columns upwardly. The membrane is held in place by a rigid cover provided with one through-hole for each column, respectively. The process for transferring liquid into the columns and from the columns into the underlying receptacle occurs as follows: an injection needle engages the cover and pushes the plate downwardly against biasing springs, into a position of sealing engagement of a lower periphery of the plate; applying vacuum within the receptacle so as/to maintain said sealing engagement, escape of said vacuum through the empty columns being prevented thanks to the membrane; displacing the needle up to a source of liquid drawing liquid from the source into a syringe to which the needle belongs; bringing back the needle above a selected column; moving the needle downwardly through the membrane; injecting the liquid into the column; waiting that the liquid is sucked by vacuum into the receptacle while the needle remains in place through the membrane, the needle being provided with an external longitudinal groove to allow air to enter the column while liquid is sucked from the column; then withdrawing the needle from the column. This process is repeated for each column, or each group of columns if the injection head is provided with more than one needle.

When one of the above steps of conditioning, loading and washing is completed, the vacuum is released so as to allow the plate to move upwardly under the action of the biasing springs. After the washing step, the carriage is displaced from the drain receptacle to above the collect receptacle, whereupon the sub-steps of lowering the plate, establishing vacuum, and then successively feeding the columns with a simultaneous sucking of the liquid from below is repeated.

Typically, instead of using a needle, there is used an array of e.g. four aligned needles so as to expedite as far as possible the completion of the process.

However, the whole procedure is relatively long in duration. Furthermore, there is a risk that a previously perforated area of the membrane is no longer leak-tight and allows substantial entry of air into another column than those being currently fed with liquid, so that the efficiency of vacuum onto the columns being currently handled may be reduced.

Movement of the carriage from above one of the receptacles to above the other receptacle is performed by inserting the needle in one of the holes of the cover, then displacing the needle horizontally so as to cause the carriage to slide into side guides or rails of a frame of the rack. This may result in contamination of the column corresponding to the hole in which the needle penetrates for such actuation.

A main object of the present invention is to remedy at least one of the above-listed disadvantages of the prior art.

Another object of this invention is to allow quicker preparation of samples for analysis.

A further object of this invention is to allow safer operation of the rack during preparation of samples for analysis.

A still further object of this invention is to allow quick and easy handling of the plate, which is usually disposable after each sample preparation, and of the underlying receptacles, the collect receptacle needing to be withdrawn form the rack when the samples are ready for analysis by chromatography.

Accordingly, there is provided a method of preparing samples for analysis, comprising the steps of:
injecting at least one liquid in individual columns of a movable plate by means of at least one movable injection needle;
displacing said plate between at least two operational positions by displacing said at least one needle while said at least one needle is in a relationship of at least indirect mutual engagement with said plate;
characterized by said mutual engagement being performed between said needles and engagement formations outside said columns.

According to this aspect of the invention, mechanically and biologically safe mutual engagement of the needle with the plate (or e.g. a carriage supporting the plate) is provided. Specific formations may be provided and selected for specific movements of the plate. Typically, different formations are provided for displacing the plate horizontally from one underlying receptacle to another underlying receptacle, and from a raised position to a lowered, sealing position above a receptacle.

Thus, according to this aspect of this invention, the needle or typically the array of e.g. 4 needles, is fully appropriate for actuating the plate between its operational positions. According to another aspect of this invention, there is provided a method of preparing samples for analysis comprising:
injecting a liquid in each column while the columns are open upwardly;
displacing said plate downwards into an at least indirect sealing engagement above an underlying receptacle;

subjecting said receptacle to vacuum thereby to retain said plate in said sealing engagement and draw liquid from all said columns into said receptacle through a stationary phase provided in said columns;

releasing said vacuum thereby to allow upward displacement of said plate out of said sealing engagement.

This method allows to dispense with the membrane and with the risk of imperfect sealing action thereof. All the columns have been fed with liquid at the end of a first stage and only then, the columns are all together subjected to vacuum from below. This is not only safer but also quicker because it is no longer necessary to wait that the content of each column is sucked before withdrawing the injection needle therefrom and bringing back the syringe to the liquid source. The consumption of vacuum is reduced because the time during which vacuum is applied is much shorter.

According to a third aspect of this invention, there is provided a rack for preparing samples for analysis, comprising:

a frame;

a slidable assembly which is slidingly mounted in the frame and is provided with a plate having a plurality of columns for receiving samples through an upper opening of said columns;

a first and a second receptacle mounted in the frame underneath the carriage;

means for selectively connecting each said receptacle with a vacuum source; said slidable assembly being movable between a first position above said first receptacle and a second position above said second receptacle, characterized by said slidable assembly being provided with engagement means for a needle, said engagement means being located outside said columns.

According to a fourth aspect of this invention, there is provided a device for preparing samples for analysis comprising:

a rack according to the first aspect;

an injection unit in turn comprising:

a) an injection head provided with at least one injection needle;

b) an actuator for three-dimensional displacement of said injection head;

c) control means for controlling said actuator whereby said head is successively brought in injection positions in which the needle registers with columns of said plate, and in plate drive positions in which said needle registers with said engagement formations and then drives said plate for a predetermined displacement.

Further features and advantages of the intention will be apparent from the following description of a non limiting embodiment.

In the drawings:

FIG. 1A is a detail of FIG. 1 at an enlarged scale;

FIG. 1B is similar to FIG. 1A, but with the plate in its raised position and the carriage ready for sliding movement;

As shown in FIGS. 1-7, the rack 5 comprises a frame 1 which is comprised of a base 2 and a sub-frame 3. The base 2 in turn comprises a base plate 4 which is adapted to rest on a supporting surface such as a table or the sole plate 61 of the device according to the invention (FIG. 10), and end-plates 6 which extend upwardly from each longitudinal end of the base plate 4 respectively.

Figure 2:
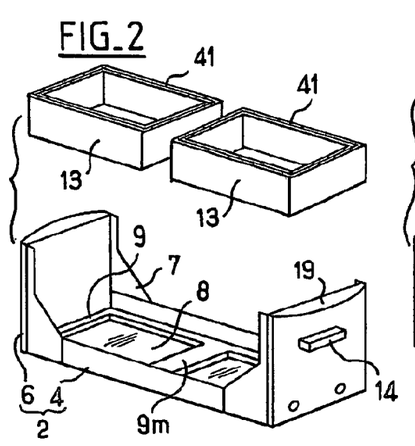
FIGS. 2 to 7 are perspective views showing six successive states of assembly of the rack.
Figure 3:
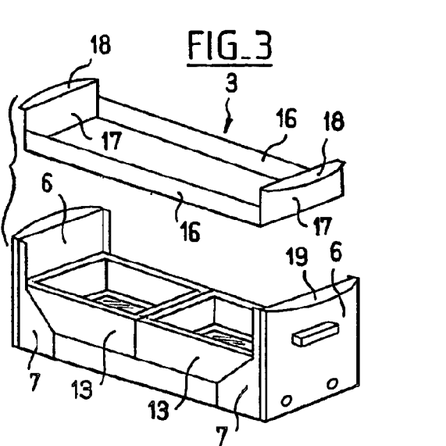

The end plates 6 are rigidly secured to the base plate 4 by means of corner-stiffeners 7 (FIG. 2).

The upper face of the base plate 4 is provided with two rectangular shallow recesses 8, each one being surrounded by a rectangular peripheral rib 9, these ribs being joined together in an area 9m along the short median line of the base plate 4. Accordingly, the recesses B are aligned along the longitudinal direction of the base plate 4 which is of a rectangular elongated shape.

Each one of the recesses B is adapted to receive and position a corresponding receptacle, i.e. a drain receptacle 11 and a collect receptacle 12. The receptacles 11, 12 are of rectangular shape so as to be capable of stable positioning in their respective recesses 8 by mere gravity.

There is furthermore provided upon the base plate 4, freely stacked thereon, two tubular spacer elements 13, each one onto a respective one of the peripheral ribs 9. The tubular spacers 13 have outer dimensions so as to just fit together between the two end plates 6 of the base 2 and between the corner stiffeners 7. Thus, though freely mounted, they are in a stable position with respect to the base plate 4, unless of course they are lifted upwardly for disassembly, as illustrated in the right-hand part of FIG. 1.

Furthermore, each end-plate 6 is provided with respective handles 14.

Figure 1:
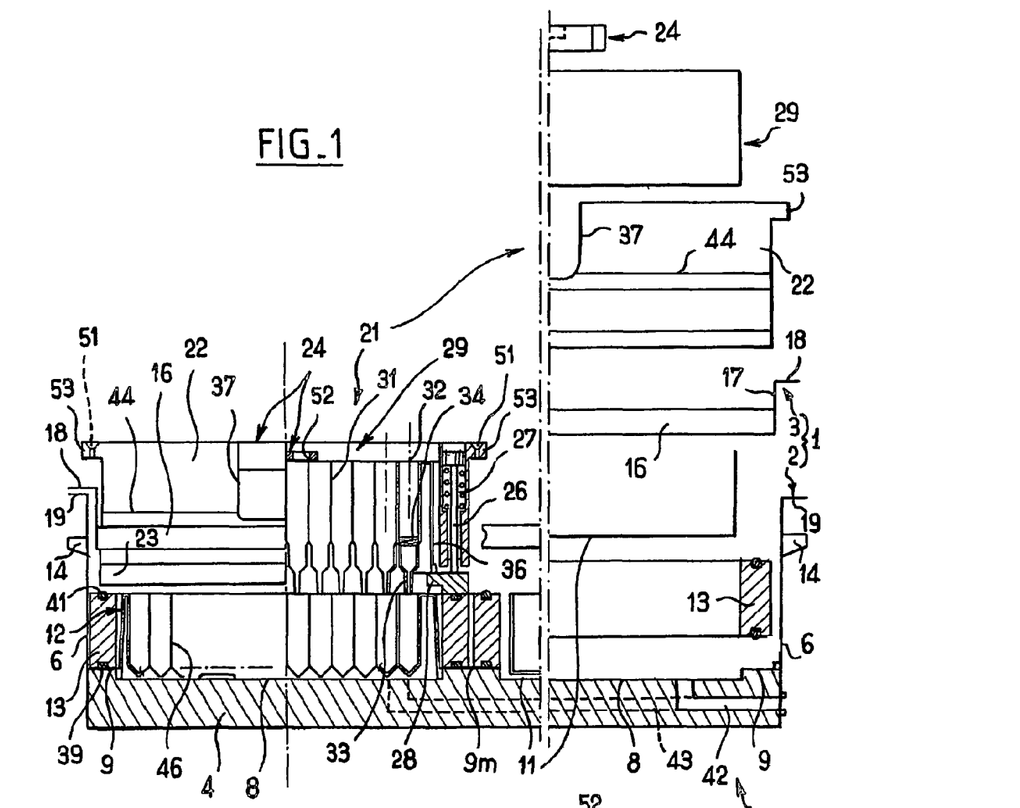
FIG. 1 is a longitudinal sectional view of a rack according to the invention, the right-hand part of the figure illustrating the method of assembling and disassembling the rack by stacking and unstacking of parts, the left part illustrating the rack in two different operational conditions with the carriage above the collect receptacle.
Figure 4:
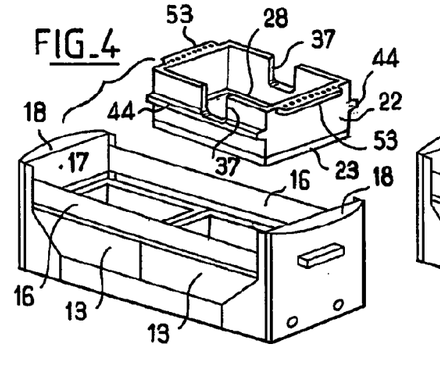
Figure 5:
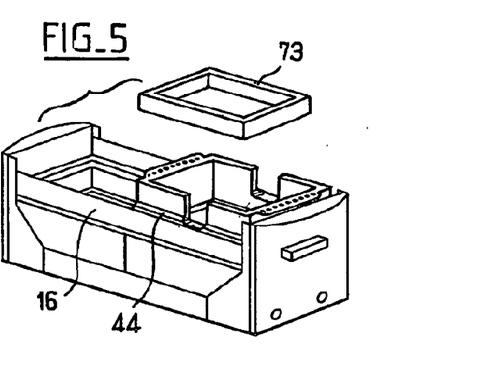
Figure 6:
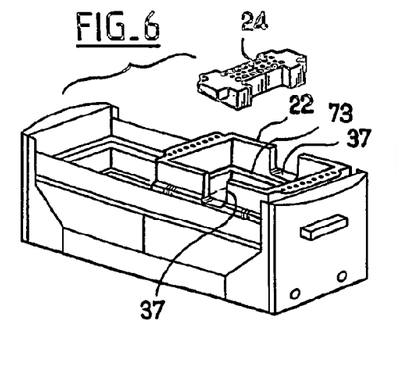
Figure 7:
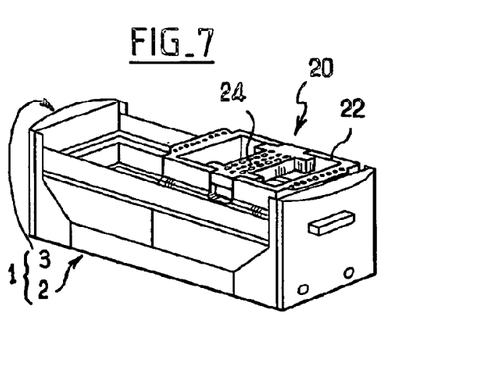
Figure 8:
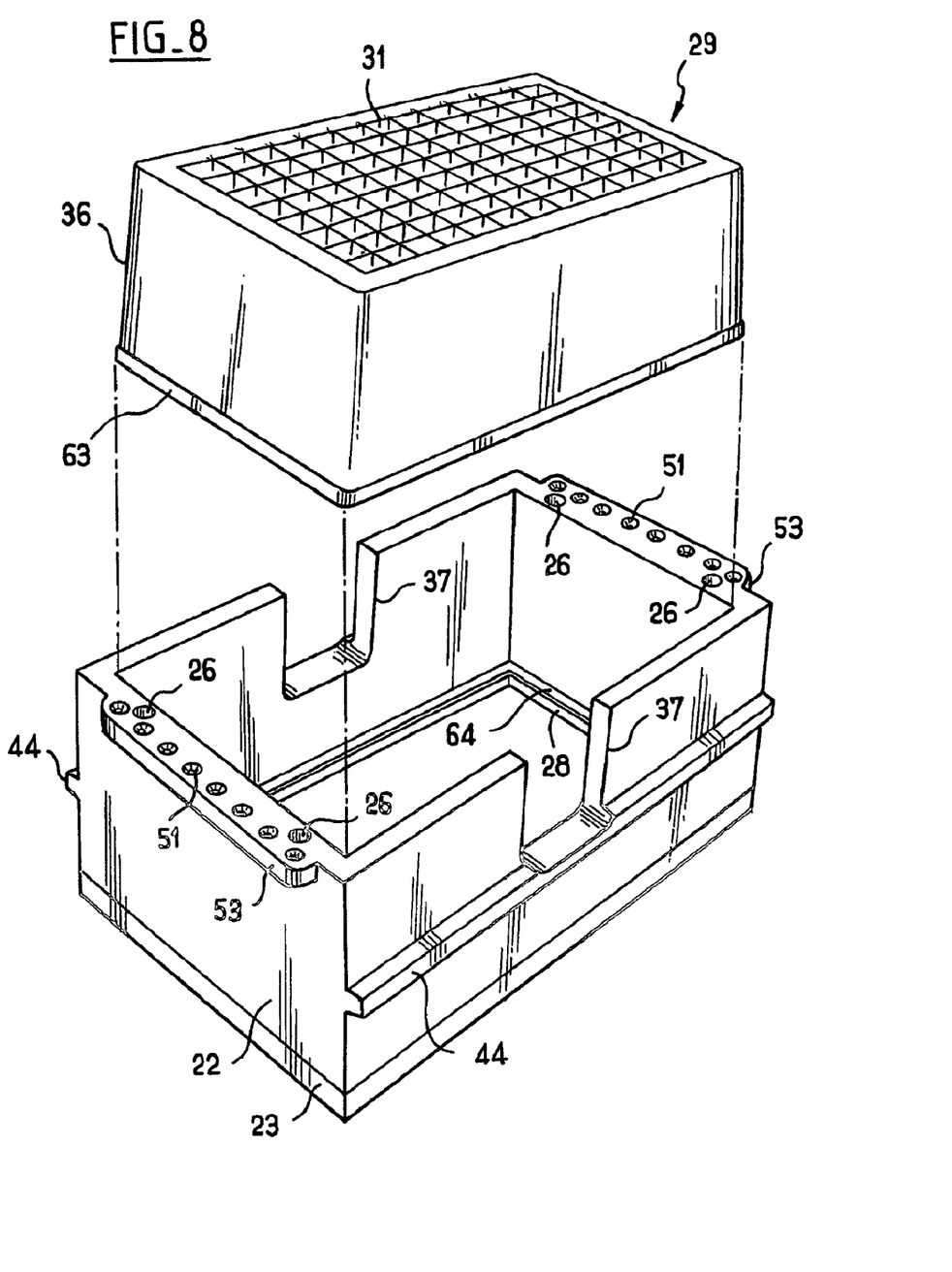
FIG. 8 is an exploded perspective view of parts of the sliding assembly.

The sub-frame 3 is essentially composed of two longitudinal guide rails 16 which are connected rigidly together by two end cross-pieces 17. As illustrated in FIG. 1 or 4, the cross-pieces 17 have upper bent edges 18 which are adapted to rest upon corresponding bent edges 19 of the endplates 6. The upper sub-frame 3 is adapted to be mounted in the base 2 by a mere stacking i.e. by a downward movement in which the sub-frame 3 fits between the two end-plates 6 and, the four corner-stiffeners 7 until the bent edges 18 come into abutment against the bent edges 19 of the end plates 6. As shown in FIGS. 1 and 4 to 7, the guide rails 16 extend then parallel to the base plate 4 at a certain distance above the upper side of the receptacles 11, 12 and of the tubular spacers 13.

The rack furthermore comprises a sliding assembly 21 which is shown in totality (though partly in section) in the left part of FIG. 1, whereas portions of the sliding assembly are redundantly shown in the assembling and disassembling condition in the right part of FIG. 1.

The sliding assembly 21 comprises a carriage 20 composed of: a body 22 which is essentially in the shape of a rectangular peripheral wall, i.e. a wall which extends along a rectangle as seen from above; a rectangular shoe 23 extending along the lower edge of the body 22; and a pusher element 24 extending along the short median line of the rectangular body 22 in the vicinity of the upper edge thereof. The short, or width-wise median line of the body 22 is parallel to the width of the base plate 4.

The shoe 23 is suspended to the body 22 by means of plungers 26 (only one is shown in FIG. 1) which are urged upwardly by springs 27 so as to bias the shoe 23 into abutment against the lower edge of the body 22 as shown in the very left part of FIG. 1. The shoe 23 has a shoulder 28 (centre of FIG. 1) which protrudes inwardly into the centre opening of the body 22.

This centre opening of the body 22 is adapted to accommodate within the carriage 20 a so-called solid phase extraction plate 29 (SPE plate 29) which is typically a single piece of plastic material and which defines an array of e.g. 8×12=96 hollow columns 31, some of which are shown in FIG. 1 and more particularly in FIGS. 1A and 1B. Each column "31 comprises an upper opening 32 which is relatively large in that it occupies the whole sectional area of the column, and a lower opening 62 (FIG. 1B) at the tip of a funnel-like position 33. The lower openings 62 are substantially flush with the lower face of the shoe 23. Within each column 31, a stationary solid phase 34 is abutted against a shoulder defining the top of the funnel like portion 33. The nature, structure and function of solid phase 34 are well-known in the art. The plate 29 also has a peripheral skirt 36 the lower edge 63 of which abuts onto a seal 64 fitted in a recess of the upper face of the shoulder 28 of the shoe 23.

The element 24 is in a resting abutment against the upper side of the SPE plate 29 and is mounted for vertical sliding movement within the body 22 of the carriage. For such vertical sliding movement, the longitudinal walls of the carriage body 22 are provided with respective notches 37 and the pusher element is provided with lateral shoulders 38 (FIG. 9) which engage the inner face of the longitudinal wall of the body 22 thereby to immobilize the pusher element 24 against movement along the width of the carriage body 22.

When the pusher element 24 is urged downwardly, it in turn urges SPE plate 29 downwardly. Due to abutment of the lower edge 63 of the skirt 36 against the seal 64 of the shoulder 28 of the shoe 23, this downward movement is transmitted to the shoe 23 until the shoe 23 abuts the underlying tubular spacer 13.

Each tubular spacer 13 is provided with a lower seal 39 along its lower periphery and an upper seal 41 along its upper periphery. The lower peripheral seal 39 cooperates with the corresponding rib 9 of the base-plate 4 and the upper peripheral seal 41 cooperates with the lower face of the shoe 23 when urged downwardly by the pusher element 24. Furthermore, a sealing contact is provided between the lower edge 63 of the skirt 36 and the seal 64 at least when the plate 29 is urged downwardly by the pusher 24. Thus, in such a situation, a closed space is realized between the base plate 4 and the plate 29 except for any passage through the columns 31 and except for a respective duct 42, 43 provided through the base plate 4 for selectively connecting each recess 8 with a vacuum source, respectively.

The longitudinal walls of the carriage body 22 are each provided with an external longitudinal rib 44 for sliding abutment against the upper edge of a respective one of the guide rails 16 while the lower part of the body 22, extending below said ribs 44, fits between the guide rails 16.

Thus, again, the slidable assembly is mounted by a mere stacking onto the frame and more particularly between the guide rails 16. Furthermore, the plate 29 is mounted by a mere stacking into the carriage body 22 until abutment against the shoulder 28 of the shoe 23, and the pusher member 24 is in turn mounted by stacking onto the plate 29 and within the notches 37.

Depending on the type of samples to be prepared, it exists different heights of plate 29. As illustrated by a comparison of FIGS. 6 and 9, there are provided according to the invention pusher elements 24 of different thicknesses. The operator selects a thicker pusher elements when the plate 29 has a lower height. There is also a possibility of inserting a distance frame 73 (FIGS. 5 and 6) between the lower edge 63 of the plate-skirt 36 and the seal 64.

The sliding assembly 21 is mounted for sliding onto the guide rails 16 between two end positions in each of which it registers with one or respectively the other of the two receptacles, 11 12, and with the corresponding tubular spacer 13.

In the first position, adapted for steps of conditioning, loading and washing, the sliding assembly 21 is above the receptacle 11 which is a drain receptacle, i.e. a simple basin in which the liquid flowing out of the columns 31 is mixed for subsequent disposal.

In its other end position, the sliding assembly 21 is above the collect receptacle 12 which is provided with one respective well 46 for each column 31 of the plate 29. Each well is open upwardly and closed downwardly.

Figure 10:
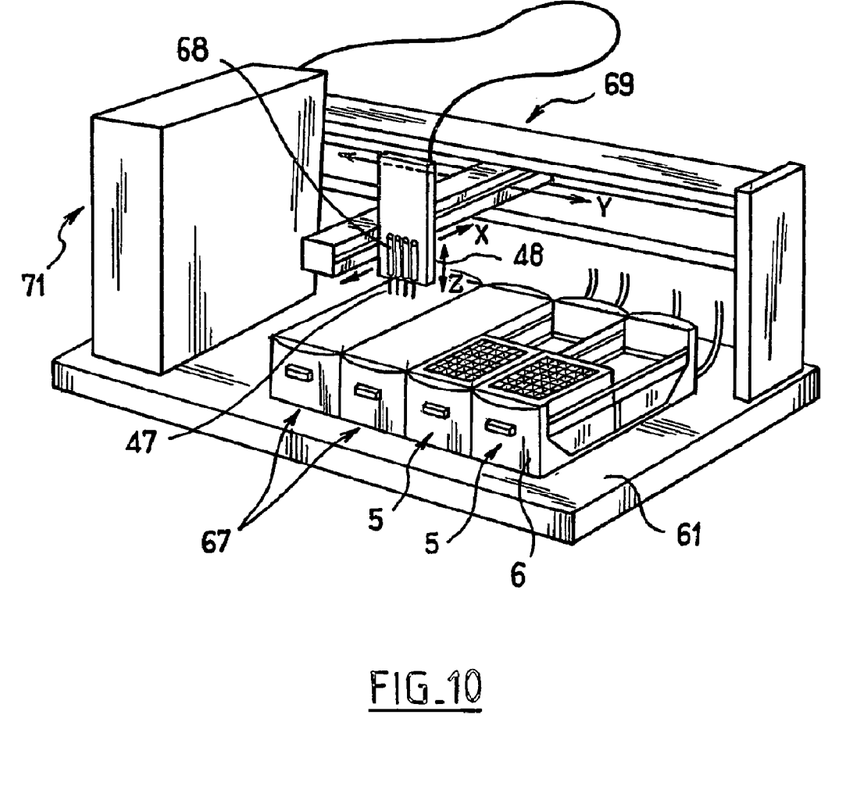
FIG. 10 is a view of the preparing device according to the invention, incorporating two racks of FIGS. 1-9 and an injection head with actuator means and control means.

The sliding assembly 21 is adapted to be actuated by the injection needles 47 of an injection head 48 of a preparing device 66 according to the invention (FIG. 10).

In the example illustrated, the injection head 48, is provided with four needles 47 aligned in a row which is parallel to the width of the rack. The spacing between the adjacent needles, which may be adjustable, corresponds to the spacing between the adjacent columns 21. The carriage 20 is provided with engagement means for the tips of the needles 47. Such engagement means comprise blind recess formations 49, having a conical shape, which are provided along a centre line of the upper face of the pusher element 24 so as to correspond with the widthwise median line of the plate 29, said median line extending between two adjacent rows of columns 31. The spacing between adjacent recesses 49 corresponds to the spacing between adjacent needles 47 of the head 48.

On either side of the row of recesses 49, there is provided a row of apertures 52 through the pusher member 24. Each aperture 52 registers with a column 31 of a row adjacent said median line.

The body 22 is provided with an outwardly protruding flange 53 along the upper edge of each of its two widthwise wall sections. The engagement means comprise, in addition to said recesses 49, recess formations 51 which are provided as two rows, each one in the upper face of one of the flanges 53. Again, the mutual spacing of the recesses 51 equals that of the needles 47 on the injection head. The recesses 51 are through holes having a conical upper entrance and a cylindrical vertical lower outlet having a diameter appropriate for sliding movement of the needles 47 therein.

FIG. 10 is a diagram of a typical arrangement of the device according to the invention. The injection head 48 is carried by a XYZ actuator 69 controlled by a control unit 71 which is connected to, or incorporates, computing means adapted to be programmed. Beneath the movement space of the injection head, the sole plate supports two racks 5, each one corresponding to FIG. 1 to 9, mounted with their longitudinal direction corresponding to the X direction of movement of actuator 69. The sole plate 61 furthermore supports two racks 67 containing one or more liquid sources. The control unit 71 is connected to the injection head 48 for controlling syringes 68 associated each with one needle 47. The device furthermore comprises a valve box 74 (FIG. 11) containing for one rack 5 two pneumatic valves 76, 77 connecting the ducts 42, 43, respectively, either to a vacuum source 78 or the atmosphere, selectively. The valves 76, 77 are controlled by the control unit 71. The program which governs operation of the control unit 71 defines the combined timings of operation of the actuator 49, the syringes 68 and the valve box 74.

The operation of the rack and of the device, and implementation of the method are as follows, with reference to FIG. 11 to 15.

The carriage 20 being in its first position above the drain receptacle 11, (FIG. 11) with the vacuum interrupted in both recesses 8 (both ducts 43, 43 connected to atmosphere by valves 76, 77), the injection head 48 performs shuttle movements (arrow 79) between a selected one of several liquid sources 67, a position above selected columns 21, and possibly a rinsing position above another liquid source. At the liquid source 67, the needles draw liquid into their respective syringes 68. Above the plate 29, each needle 47 discharges the liquid of its syringe into a respective column 31. During this process, all the columns 31 are open upwardly.

Figure 11:
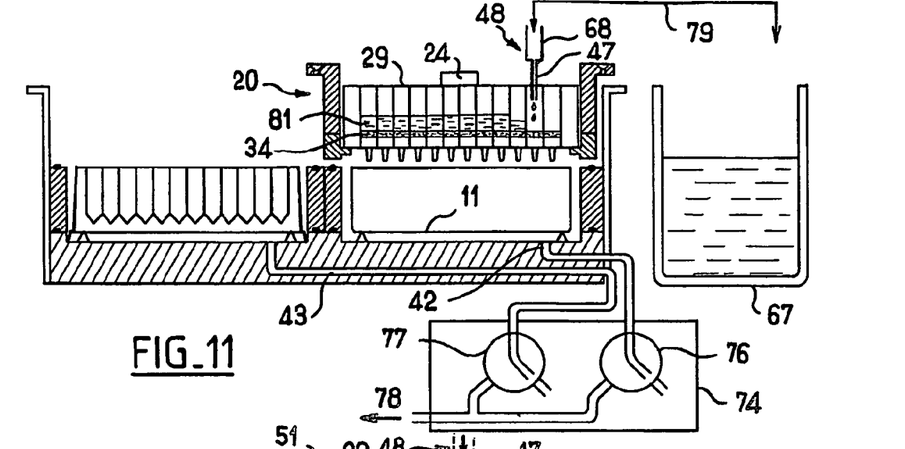
FIGS. 11-15 are diagrams illustrating successive operating stages of the preparing device and respectively successive steps of the method according to the invention.
Figure 12:
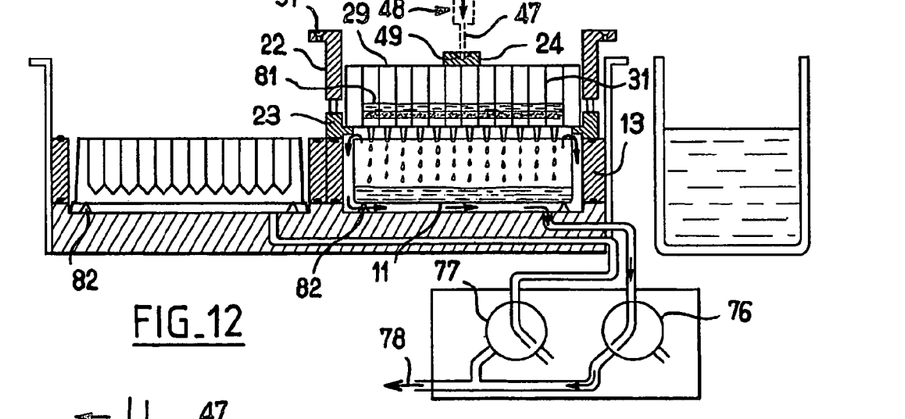
Figure 13:
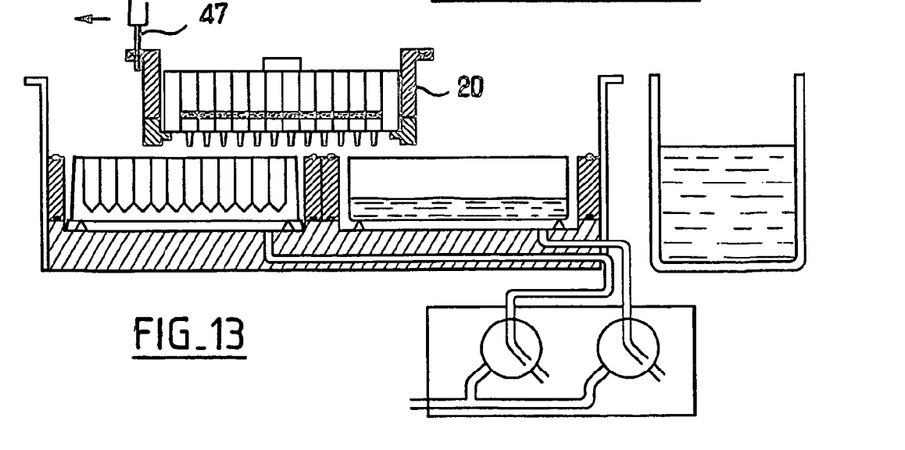
Figure 14:
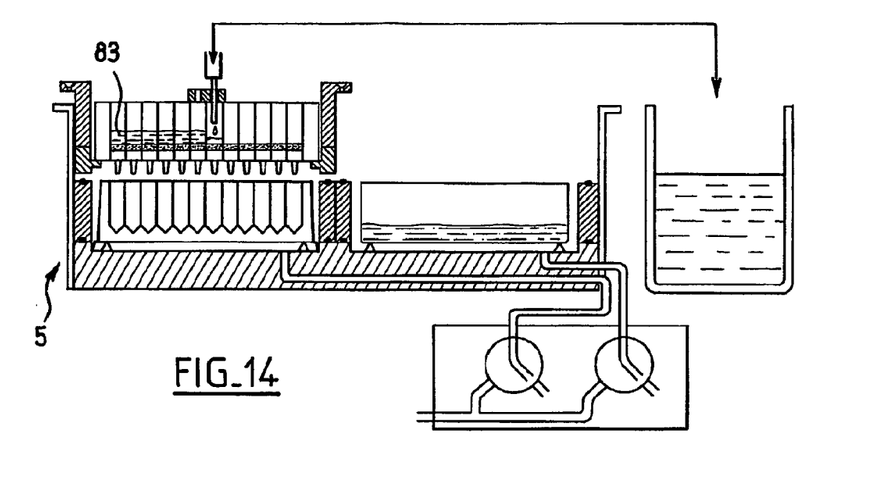
Figure 15:
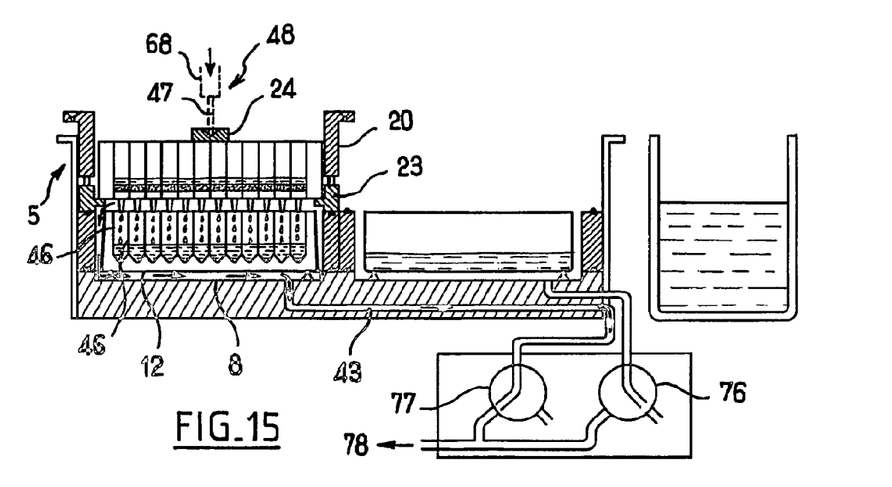

Each time, the head 48 is moved by the actuator means 69, controlled by the control unit 71 according to the above mentioned program, in the X and Y horizontal directions between above the plate 29 and above the liquid source 67, and then in the Z direction to dip the needles 47 into the liquid source 67 and into the columns 31 respectively, for the liquid sucking and discharging respectively, and then in the upward direction out of the source 67 and out of the columns 31 respectively. For feeding those columns which are located below the pusher element 24, the needles proceed through the apertures 52.

Figure 9:
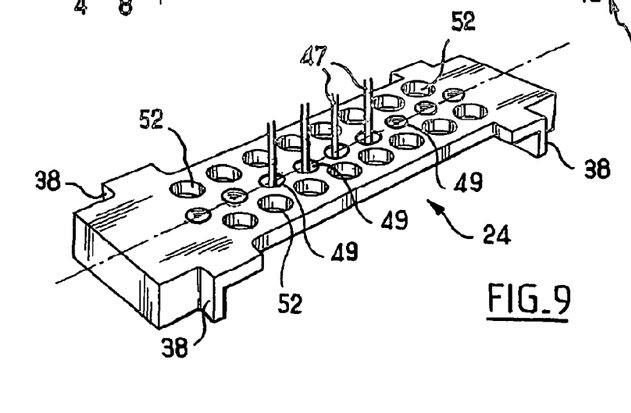
FIG. 9 is a perspective view of the pusher element cooperating with needles.

When all the columns are provided with liquid 81, the injection head is moved to above" four of the recesses 49 and then in the downward direction until the situation shown in FIG. 9 in which the needles 47 engage the recesses 49 of the pusher element 24 is realised. Then, the needles 47 urge the pusher element 24 downwardly together with the plate 29 and shoe 23 until the shoe 23 abuts the spacer 13 (FIG. 11). Simultaneously, while the top of all columns is still open, valve 77 is controlled to connect duct 42 with the vacuum sources 78, whereby the vacuum is applied within the receptacle 11 and thus within the lower part of the columns 31 to simultaneously draw liquid from all the columns 31 together into the receptacle 11. It is apparent in FIG. 12 that receptacles 11 and 12 are supported on bosses 82 and with some small lateral play to allow vacuum, when present in recesses 8, to safely reach the underside of plate 29. As soon as vacuum is applied above receptacle 11, the needles can be moved upwardly because the plate 29 remains in its lower position due to the under-pressure experienced by its lower face. Vacuum can not escape because all columns 31 contain liquid 81. Once liquid extraction is completed the vacuum is interrupted and the shoe 23 moves back upwardly under the biasing effect of springs 27 (FIG. 1B). Either a second liquid processing is realized above the same receptacle 11 or, if it was the last processing intended to occur above receptacle 11, the injection head is moved to above four of the recesses 51, is lowered into engagement of the needles 47 through these four recesses 51 (FIG. 1B), is moved (FIG. 12) in the X direction (lengthwise of the base 2, arrow 72 in FIG. 1B) to drive the carriage 20 horizontally until the carriage is above the collect receptacle 12, and the head 48 is then moved upwardly for disengaging the needles 47 from the recesses 51.

Then the procedure of successively feeding the columns with liquid, until all the columns contain liquid (FIG. 14), pushing down the plate 29 into sealing engagement with the base 4 via the shoe 23 and spacer 13 (FIG. 15), subjecting the area below the plate 29 to vacuum 78 by an appropriate control, this time through valve 77 and duct 43, and releasing vacuum, is resumed. This time, the content of each column 31 is collected in a respective one of the wells 46 (FIGS. 1A and 15), for separate analysis of the content of each well. Again, all this occurs while all the columns 31 are open upwardly.

Then, the rack 5 can be dismounted by stacking off the pusher element 24, the plate 29, the carriage body 22 with shoe 23, the sub-frame 3, the spacers 13, the receptacles 11, 12. The plate 29 is normally intended for disposal, the receptacle 12 for analysis of the content of the wells, and the other parts for cleaning in view of re-use.

Said formations 49 are in a staggered relationship with said apertures 52 thereby to coincide with centers of virtual squares the angles of which are the centers of four columns 21.

There is no interference between the formations 49 and the apertures 52. The conical shape of the recesses 49 perform a self centering of the needles so as to keep them as far as possible from the apertures 52 and more generally from the columns 31, so that no liquid adhering to the needles can pollute the columns during actuation of the plate 29.

The recesses 51 on the flanges 53 are also far enough from the upper opening of the columns for fulfilling this condition of biological safety. Being open downwardly, the recesses 51 automatically eliminate residual liquid. The recesses 49, 51 are sufficiently numerous so that the program may select the most appropriate recesses for each plate actuation taking into account that the actuation effort should preferably not create a risk of jamming or seizure of the carriage, and the travel of the needles towards the recesses should be as short as possible starting from the previous operating site of the needles, as well as the travel from the recesses towards the next operating site of the needles. The number of recesses 49, 51 of each kind allows for use of e.g. eight needles on a corresponding injection head (not shown).

The invention is not limited to the described embodiment. It is e.g. contemplated that the carriage 20 may accommodate plates having columns of different sectional areas, so that the distance between adjacent columns may in certain cases be different from the distance between adjacent recesses 49 or between adjacent recesses 51. This can be accommodated by adjusting the distance between the needles 47 during operation by means of an appropriate control program.

What is claimed:

1. A rack for preparing samples for analysis, comprising:
   a frame;
   a sliding assembly configured to slide in said frame, and comprising a plate having a plurality of columns for receiving samples and engagement means located outside said columns for engaging a needle;
   a first and a second receptacle mounted in said frame underneath said sliding assembly; and
   means for selectively connecting at least one of said first receptacle and said second receptacle with a vacuum source,
      wherein said sliding assembly is configured to move between a first position above said first receptacle and a second position above said second receptacle, and
      wherein each of said plurality of columns comprises an upper column portion above a solid phase and a lower column portion below said solid phase, said upper column portion above said solid phase configured to open in an unobstructed manner to the atmosphere, and said lower column portion below said solid phase configured to reduce in diameter in the direction of a lower opening.

2. A rack according to claim 1, wherein said sliding assembly further comprises a carriage removably supporting said plate, and wherein said engagement means are provided on said carriage.

3. A rack according to claim 2, wherein said carriage comprises a body having an upper edge extending along at least part of the periphery of said plate, and wherein at least part of said engagement means is provided on said upper edge.

4. A rack according to claim 3, wherein said engagement means comprise a row of recesses along a transverse edge belonging to said upper edge and extending transversely to the sliding direction of said carriage.

5. A rack according to claim 2, wherein said carriage comprises a body in which said plate is mounted for limited downward movement against biasing springs, and a pusher element which is mounted for vertical movement in abutment above said plate and is provided with at least part of said engagement means.

6. A rack according to claim 5, wherein said pusher element is provided with apertures which register with one or more of said columns underlying said pusher element.

7. A rack according to claim 5, wherein said pusher element extends along a median line of said plate.

8. A rack according to claim 2, wherein said rack is configured to be assembled by successive stacking of parts and to be disassembled by successively unstacking of said parts thereby allowing for rapid removal of a used plate and receptacles, and quick insertion of a new plate and receptacles.

9. A device for preparing samples for analysis comprising:
a rack including:
   a frame;
   a sliding assembly configured to slide in said frame, and comprising a plate having a plurality of columns for receiving samples and engagement means located outside said columns for engaging a needle;
   a first and a second receptacle mounted in said frame underneath said sliding assembly; and
   means for selectively connecting at least one of said first receptacle and said second receptacle with a vacuum source,
      wherein said sliding assembly is configured to move between a first position above said first receptacle and a second position above said second receptacle, and
      wherein each of said plurality of columns comprises an upper column portion above a solid phase and a lower column portion below said solid phase, said upper column portion above said solid phase configured to open in an unobstructed manner to the atmosphere, and said lower column portion below said solid phase configured to reduce in diameter in the direction of a lower opening; and
an injection unit including:
   an injection head provided with at least one injection needle;
   an actuator for three-dimensional displacement of said injection head; and
   control means configured to control said actuator, wherein said injection head is configured to move to injection positions in which said needle registers with columns of said plate, and further configured to move to plate-drive positions in which said needle registers with said engagement means and drives said plate for a predetermined displacement.

10. A device according to claim 9, wherein said sliding assembly further comprises a carriage removably supporting said plate, and wherein said engagement means are provided on said carriage.

11. A device according to claim 10, wherein said carriage comprises a body having an upper edge extending along at least part of the periphery of said plate, and wherein at least part of said engagement means is provided on said upper edge.

12. A device according to claim 11, wherein said engagement means comprise a row of recesses along a transverse edge belonging to said upper edge and extending transversely to the sliding direction of said carriage.

13. A device according to claim 9, wherein said carriage comprises a body in which said plate is mounted for limited downward movement against biasing springs, and a pusher element which is mounted for vertical movement in abutment above said plate and is provided with at least part of said engagement means.

14. A device according to claim 13, wherein said pusher element is provided with apertures which register with one or more of said columns underlying said pusher element.

15. A device according to claim 13, wherein said pusher element extends along a median line of said plate.

16. A device according to claim 9, wherein said rack is configured to be assembled by successive stacking of parts and to be disassembled by successively unstacking of said parts thereby allowing for rapid removal of a used plate and receptacles, and quick insertion of a new plate and receptacles.

* * * * *